US00PP30212P2

(12) United States Plant Patent
Kinosian

(10) Patent No.: US PP30,212 P2
(45) Date of Patent: Feb. 19, 2019

(54) GRAPEVINE NAMED 'ROYAL RED'

(50) Latin Name: *Vitis vinifera*
Varietal Denomination: Royal Red

(71) Applicant: Mt. View Farming, Inc., Tulare, CA (US)

(72) Inventor: Todd Alan Kinosian, Tulare, CA (US)

(73) Assignee: Mt. View Farming, Inc., Tulare, CA (US)

( * ) Notice: Subject to any disclaimer, the term of this patent is extended or adjusted under 35 U.S.C. 154(b) by 0 days.

(21) Appl. No.: 15/731,857

(22) Filed: Aug. 15, 2017

(51) Int. Cl.
*A01H 5/08* (2018.01)

(52) U.S. Cl.
USPC ..... Plt./205

(58) Field of Classification Search
USPC ..... Plt./205
See application file for complete search history.

*Primary Examiner* — Annette H Para
(74) *Attorney, Agent, or Firm* — Baker Manock & Jensen, PC; Eric C Cole

(57) ABSTRACT

A new and distinct variety of grapevine named 'Royal Red' particularly characterized by its large ovoid-shaped, blush red-colored seedless berries that mature in mid-August, approximately one to two weeks earlier than 'Scarlet Royal' (U.S. Plant Pat. No. 16,229) when grown in the San Joaquin Valley of Central California.

4 Drawing Sheets

Latin name of the genus and species of the plant claimed: The plant claimed relates to a new and distinct variety of *Vitis vinifera.*

Variety denomination: The plant claimed shall be known as 'Royal Red'.

CROSS REFERENCE TO RELATED APPLICATIONS

The present application is not the subject of a related application.

STATEMENT OF ANY FEDERALLY-SPONSORED RESEARCH AND DEVELOPMENT

The present invention is not subject of Federally-sponsored research or development.

BACKGROUND OF THE INVENTION

The present invention comprises a new and distinct cultivar of grapevine botanically known as *Vitis vinifera* and hereinafter referred to as grapevine named 'Royal Red'. As used herein, 'grapevine' refers to all plant parts including, vines, canes, tendrils, leaves, fruit and roots of the grapevine named 'Royal Red'. Grapevine named 'Royal Red' is the result of an effort to produce an early ripening, red-colored seedless grape with fruit characteristics superior to commercial cultivar 'Scarlet Royal' (U.S. Plant Pat. No. 16,229). The new variety is the result of hybridization of 'Autumn Royal' (unpatented), the pollen parent, and 'Cabernet Sauvignon' (unpatented), the seed parent. The new variety was first hybridized in Plainview, Calif. in the Spring of 2008. Vines of the new variety were asexually propagated in the Fall of 2010 by cutting cross-pollinated dormant wood from plants and grafting to 'Freedom' (unpatented) rootstock in a variety block located in Tulare, Calif. In 2018 the new variety was planted as rooted cuttings in a variety block located in Tulare, Calif. The present invention has been found to retain its distinctive characteristics through successive asexual reproductions.

Grapevine named 'Royal Red' differs from its female parent 'Cabernet Sauvignon' (unpatented) in that grapevine named 'Royal Red' has large ovoid shaped, blush skinned seedless berries, whereas the female parent 'Cabernet Sauvignon' (unpatented) has small round shaped, black seeded berries. Grapevine named 'Royal Red' differs from its male parent 'Autumn Royal' (unpatented) in that grapevine named 'Royal Red' has ovoid shaped, blush skinned berries, whereas the male parent 'Autumn Royal' (unpatented) has ovoid shaped, dark purple to black berries. Grapevine named 'Royal Red may be compared to the commercial cultivar 'Scarlet Royal' (U.S. Plant Pat. No. 16,229), however, grapevine named 'Royal Red' has certain distinguishing characteristics. Grapevine named 'Royal Red' differs from the commercial cultivar 'Scarlet Royal' (U.S. Plant Pat. No. 16,229) in that the berry clusters produced by grapevine named 'Royal Red' are noticeably smaller than the berry clusters produced by the commercial cultivar 'Scarlet Royal' (U.S. Plant Pat. No. 16,229). The berries produced by grapevine named 'Royal Red' are larger in size than the berries produced by the commercial cultivar 'Scarlet Royal' (U.S. Plant Pat. No. 16,229) whereby the average berry size for grapevine named 'Royal Red' is 8 grams and the average berry size for the commercial cultivar 'Scarlet Royal' (U.S. Plant Pat. No. 16,229) is 5.8 grams. The berries produced by grapevine named 'Royal Red' mature in mid-August, approximately one to two weeks earlier than 'Scarlet Royal' (U.S. Plant Pat. No. 16,229) when grown in the San Joaquin Valley of Central California.

SUMMARY OF THE INVENTION

The following are the distinguishing characteristics when grown under normal cultural practices but without the use of plant growth regulators or girdling in the Visalia area of Tulare County:

1. Red seedless table grape harvested in August with an unusually large natural berry averaging 8 grams;
2. Harvest is one or two weeks earlier than 'Scarlet Royal' (U.S. Plant Pat. No. 16,229) which is a cultivar most similar to grapevine named 'Royal Red';
3. Exceptionally good eating characteristic: firm texture, juicy, sweet, and neutral flavor with no hint of bitterness when fully mature;
4. Cluster size averages 1 to 1½ pounds and clusters are naturally loose to well filled, but not tight;
5. Seed rudiments are small, soft, and not detectable when berry is consumed;
6. Fasciated shoots are more prevalent than typically found; and
7. Stamens are partially reflexed.

DESCRIPTION OF THE DRAWINGS

This new grapevine is illustrated by the accompanying photographs which show fruit clusters, leaves, canes, and tendrils. The colors shown are as true as can be reasonably obtained by conventional photographic procedures. The photographs were taken from a plant about 5 years-old, grown in a field near Visalia, Calif. in 2016.

DETAILED BOTANICAL DESCRIPTION OF THE PLANT

Figure 1:
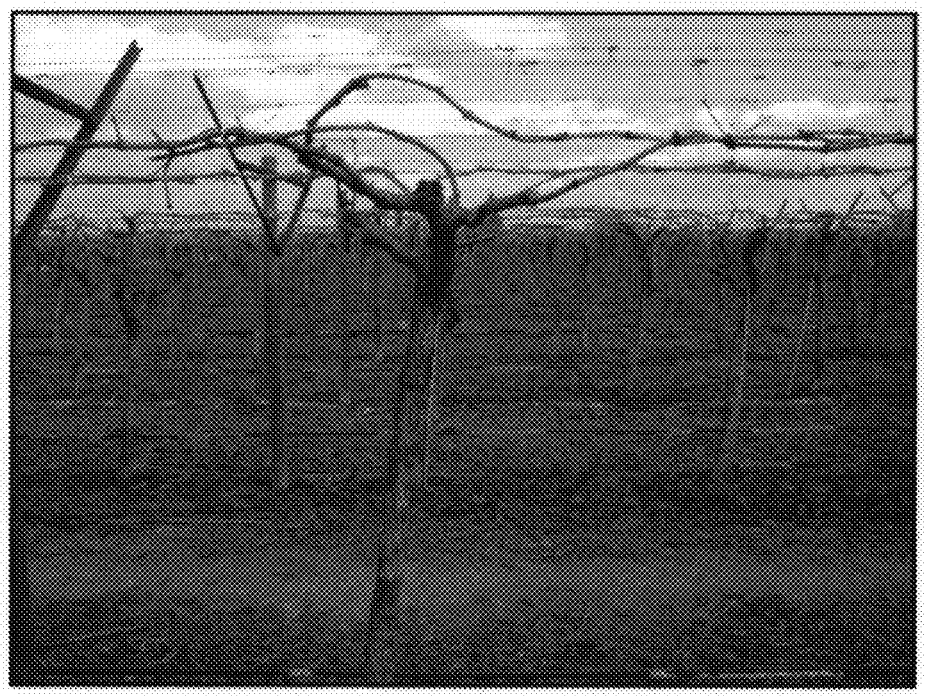
FIG. 1 Dormant vine, head trained, caned pruned, wide open gable trellis.
Figure 2:
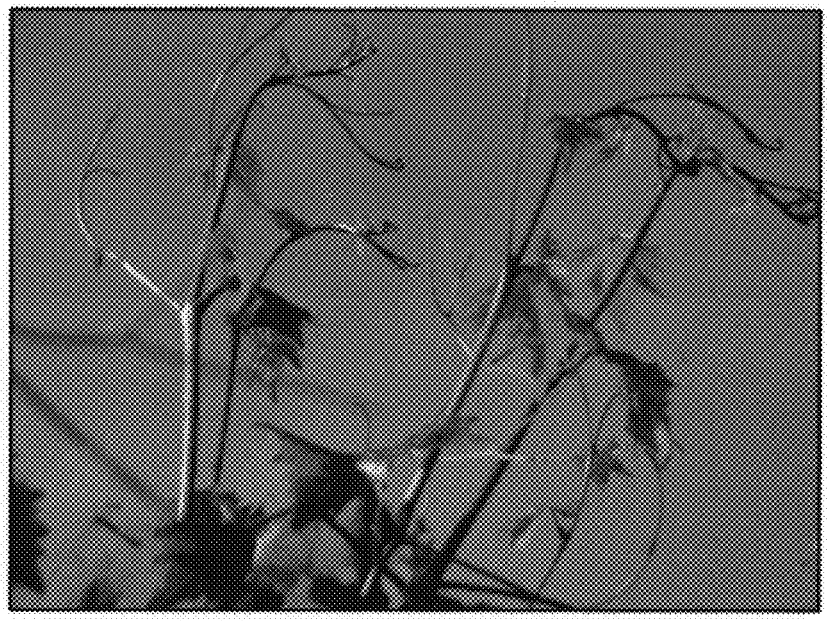
FIG. 2 Young shoot a few day prior to bloom.
Figure 3:
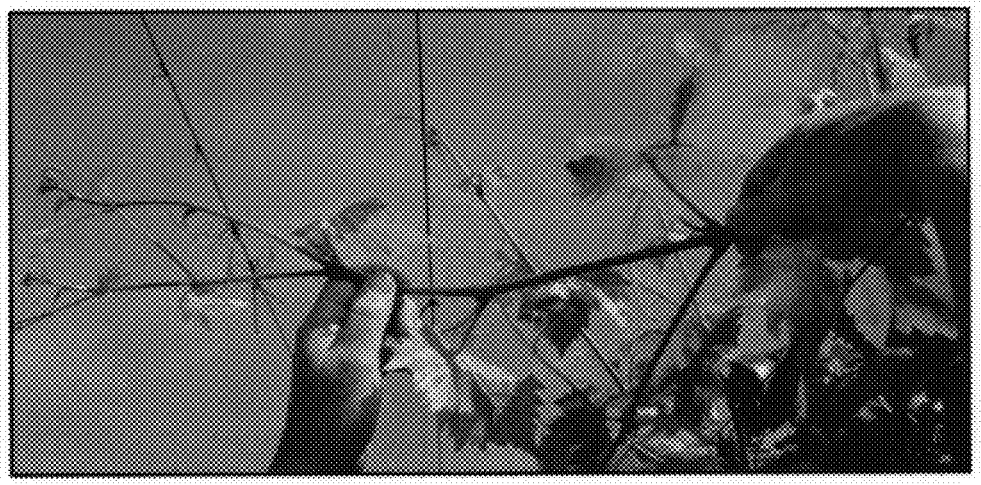
FIG. 3 Bifurcated shoot.
Figure 4:
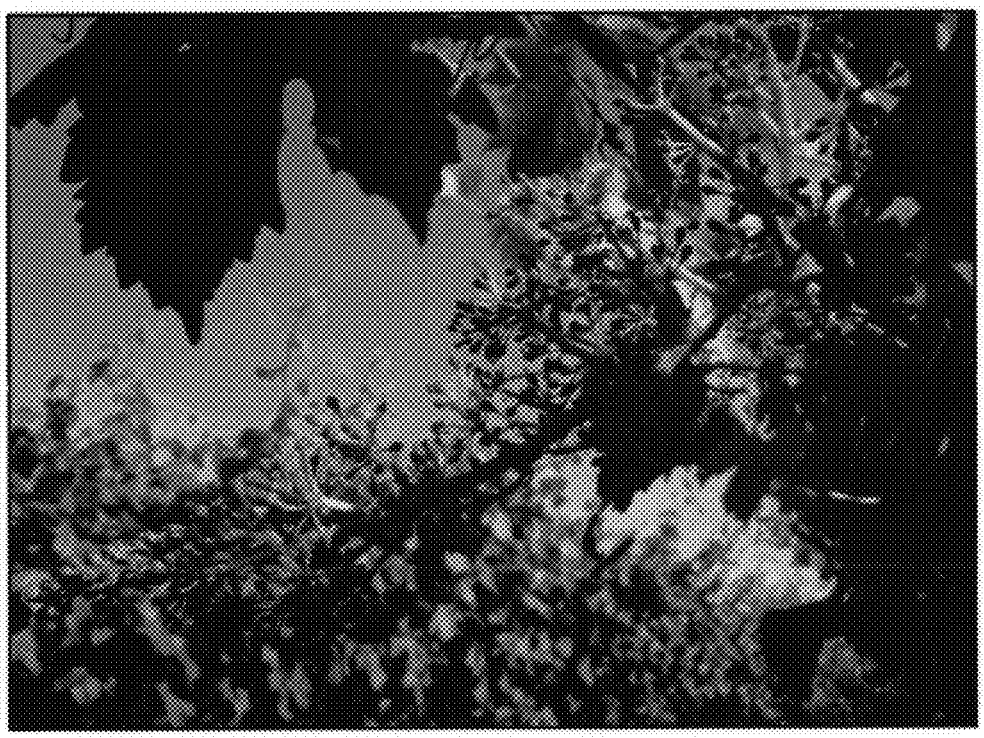
FIG. 4 Inflorescence noting tendril on peduncle.
Figure 5:
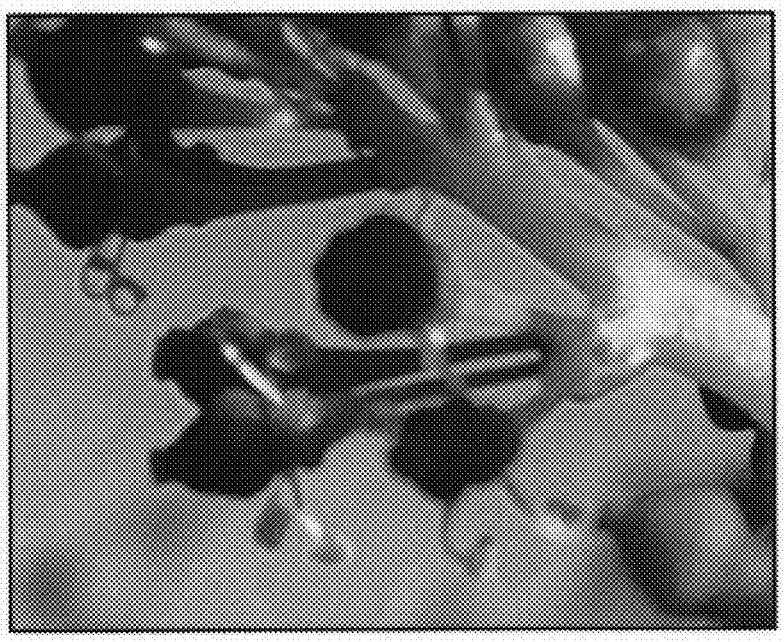
FIG. 5 Stamens that are partially reflexed.
Figure 6:
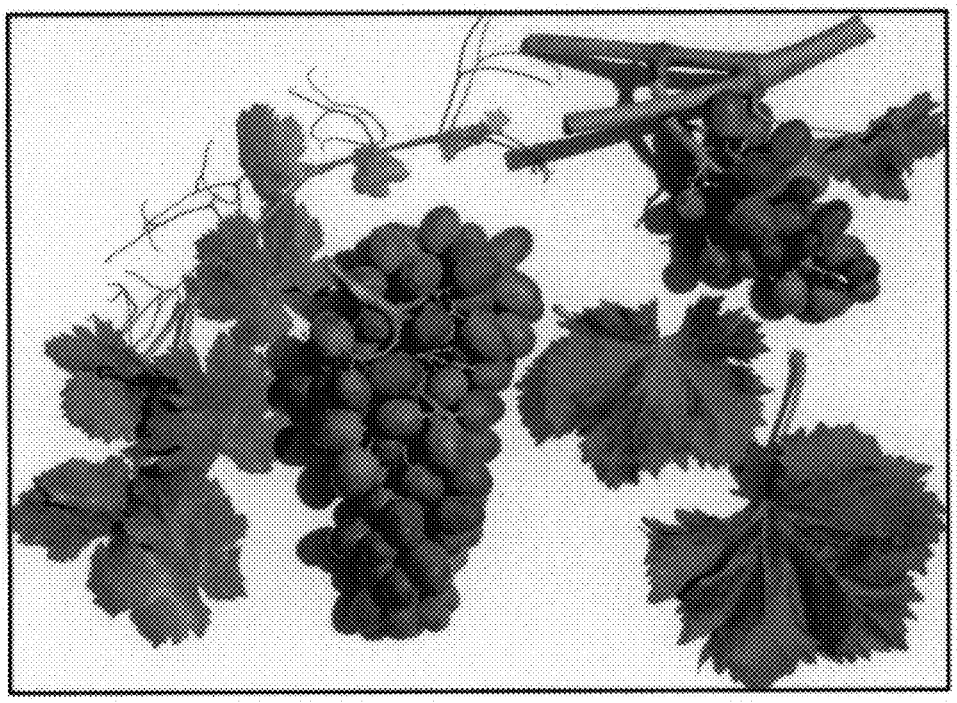
FIG. 6 Primary and secondary clusters along with immature and mature leaves.
Figure 7:
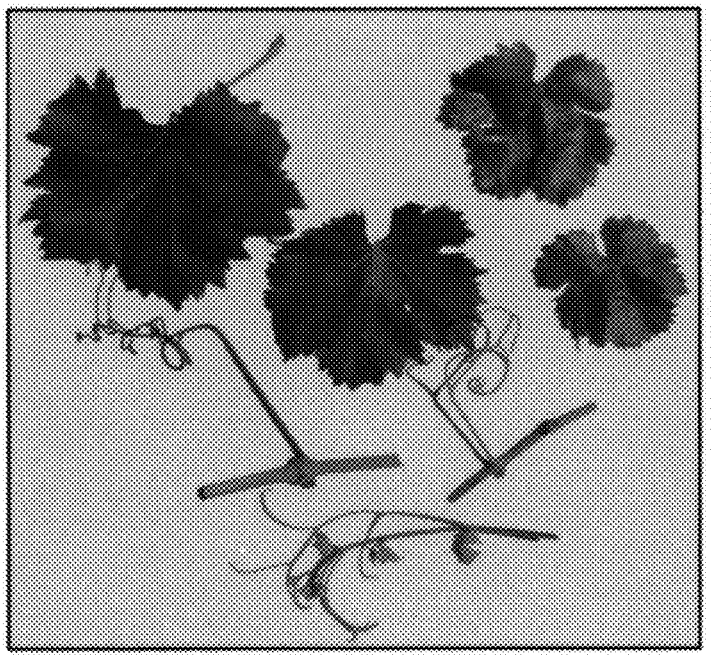
FIG. 7 Mature and immature leaves along with mature and immature tendrils.
Figure 8:
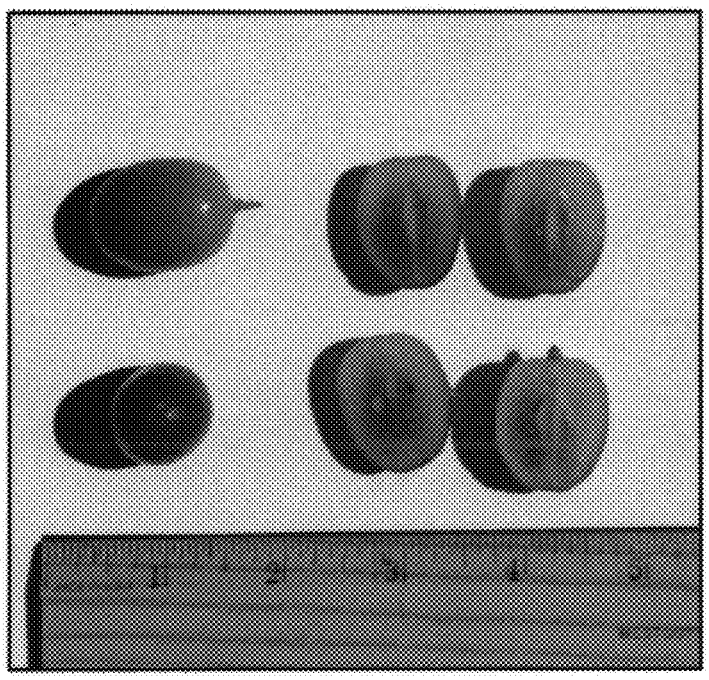
FIG. 8 Berries side and top view and sectioned to show rudimentary seeds.

The following detailed description sets forth the distinctive characteristics of grapevine named 'Royal Red'. Descriptions apply to 5 year old grapevines of 'Royal Red' grown in a field near Visalia, Calif. in 2016. These descriptions are believed to apply generally to the new variety grown under similar circumstances elsewhere. Fruit characteristics were natural (no growth regulators or girdling). All color references were under natural light. Color code designation are from Munsell Color Charts for Plant Tissue by Munsell Color, 617 Little Britain Rd., New Windsor, N.Y. 12553-6148 1977 revision. Tendril distribution is indicated by 0s and 1s; whereas, 0 is a node without a tendril and 1 is a node with a tendril.

Classification:

*Family*.—Vitaceae.

*Botanical name*.—*Vitis vinifera*.

*Variety name*.—'Royal Red'.

Plant:

*Plant habit and growth*.—Semi erect shoot growth; 30% of primary shoots bifurcated at 5th or 6th node; laterals are present on 20% of leaf axes, mostly showing beyond the 5th node from the shoot base. Laterals are very small, averaging 2.0 cm.

*Size*.—Age at maturity: 4 years. Height (at maturity): Trunk head height=56 inches (140 cm). Width (at maturity): Canopy width=10 feet (300 cm); Height (at maturity): Canopy height=76 inches (190 cm). Vigor: Medium high. Productivity: Medium low.

*Rootstock*.—Vines on own roots.

Trunk:

*Size*.—Diameter: 6.8 inches (17 cm) measured 2 feet (60 cm) above floor.

*Surface texture*.—Rough.

*Color*.—Interior, 5YR 4/6; Exterior, 7.5YR 6/2.

Canes:

*Size*.—Diameter: Diameter at $2^{nd}$ node: 0.4 to 0.5 inches (10 to 13 mm). Length: 10 feet (300 cm).

*Surface texture* (*mature cane*).—Smooth, slightly ribbed.

*Surface texture* (*immature cane*).—Smooth, slightly ribbed.

*Form* (*woody shoot cross section form*).—Pith in center with diaphragm at nodes.

*Color* (*mature*).—4 months, 7.5YR 7/6.

*Color* (*immature*).—4 weeks, 5GY 6/6, slight anthocyanin, 10R 4/6.

*Internode length* (*upper mature sun cane*).—4 to 4.8 inches (10 to 12 cm).

Time of bud burst: 70% on March 20, relatively late compared to most other table grape cultivars.

Tendrils:

*Form*.—Mostly trifid.

*Size*.—Medium large.

*Length*.—8.8 to 11.2 inches (22 to 28 cm).

*Diameter*.—0.1 to 0.14 inches (2.5 to 3.5 mm).

*Texture*.—Smooth with slight ribbing.

*Color* (*mature*).—3 weeks, 2.5GY 6/6.

*Anthocynanin* (*mature*).—10R 4/8, very slight at base.

*Color* (*immature*).—1 week, 2.5GY 6/4.

*Anthocyanin* (*immature*).—5R 7/6, very slight towards base.

Growing tips (young shoot):

*Pubescence*.—Very slight cobwebby.

*Color*.—2.5 GY 7/4.

*Anthocyanins*.—Absent.

*Shape*.—Half to wide open.

*Apex*.—Normal/triangular.

Leaves:

*Shape*.—Pentagonal.

*Apex*.—Pointed.

*Base*.—Rounded.

*Margin*.—Irregular teeth.

*Length of teeth on margin*.—0.12 to 0.6 inches (3 to 15 mm) 30% of teeth are large.

*Shape of teeth on margin*.—Pointed, both sides slightly convex.

*Texture* (*mature leaf*).—Upper surface: Slightly bullate, mostly glabrous, shiny. Lower surface: Glabrous, dull.

*Size*.—Immature, length: 10 to 14 days ($4^{th}$ leaf from shoot tip), 2.4 to 3.2 inches (6 to 8 cm). Immature, width: 10 to 14 days ($4^{th}$ leaf from shoot tip), 3.6 to 4.8 inches (9 to 12 cm). Mature, length: 3 to 4 weeks, 4.4 to 5.2 inches (11 to 13 cm). Mature, width: 3 to 4 weeks, 6 to 6.8 inches (15 to 17 cm).

*Color, immature leaf*.—Upper surface: 5GY 5/6. Lower surface: 5GY 6/6.

*Color, mature leaf*.—Upper surface: 5GY 4/6. Lower surface: 5GY 5/10.

*Venation*.—Pattern: Upper surface veins are flat; those on lower surface are raised. Color: Slight anthocyanin on base of primary veins 10R 6/8. Upper surface: 5GY 7/6. Lower surface: 5GY 7/4.

*Petiolar sinus*.—Mostly wide open but 10% half open and 10% very wide open.

*Petiole*.—Length: Average 3.4 inches (8.5 cm). Diameter: Average 0.12 inches (3 mm). Color: 5GY 7/8 with very slight anthocyanin, 10R 6/8.

Flower cluster:

*General description and location*.—Located $4^{th}$ to $5^{th}$ node; no doubles on shoots; some bifurcation; medium size.

*Quantity of inflorescences per cluster*.—Average 1800.

*Size*.—Length: 7.2 inches (18 cm). Width: With laterals spread, 8 inches (20 cm); not spread, 3.2 inches (8 cm).

*Peduncle*.—Length: Irregular, ranging from 0.4 to 2 inches (1 to 5 cm). Large tendril sometimes attached to peduncle.

*Inflorescences*.—Hermaphroditic.

*Stamens*.—Partially reflexed (shepherd crook), 0.06 inches (1.5 mm) length.

*Anthers*.—Non-descript.

*Date of bloom*.—50% on May 6, 2016.

*Pollen amount*.—Moderate with yellow to creamy color, 5Y 8/6.

*Calyptra*.—5 segments with complete separation.

*Calyptra color*.—5GY 5/10.

Fruit:

*Time of year of commercial harvest and shipment*.—Mid-Season (August).

*Cluster* (*primary bunches*).—

*Generally size*.—Large.

*Length* (*without peduncle*).—Average: 9.2 inches (23 cm).

*Width*.—Wings spread: 10 inches (25 cm); not spread: 7.6 inches (19 cm).

*Density*.—Medium loose.

*Peduncle length*.—Average: 1.6 inches (4 cm).

*Peduncle diameter*.—Average 0.32 inches (8 mm).

*Peduncle color*.—5GY 6/8 Note: the base of peduncle once matured and woody had a color of 10R 5/4.

*Number of berries per cluster*.—Average 85.

*Berry*.—Size: Large, average 0.26 ounces (8 grams). Shape: Ovoid. Uniformity: Medium uniformity. Brix content: 19° brix. Size: Diameter: 0.88 inches (22 mm). Length: 1.12 inches (28 mm). Skin color: Blush, not a deep red, 10R 4/10. The styler end (10% of total berry) is yellow green, 2.5GY 7/4. Pedicel: Length: 0.23 to 0.4 inches (6 to 10 mm). Diameter: 0.04 inches (1 mm). Color: 5GY 7/6. Strength of attachment to berry: Good. Berry Firmness: Medium firm. Averaged 200 g using a Wagner pressure tester with 3 mm probe.

*Cluster* (*secondary bunches*).—Generally size: Medium averaging 0.3 pounds (144 g). Length (without peduncle): Average 3.0 inches (7.5 cm). Width: Average 3.2 inches (8 cm). No wings. Density: Medium. Peduncle length: Average 4.2 inches (10.5 cm.). Peduncle diameter: Average 0.12 inches (3 mm). Peduncle color: 5GY 7/6. Number of berries per cluster: Average 24. Berry: Size: Large; 0.21 ounces (6 g). Shape: Ovoid, but not quite as elongated as berries on primary cluster. Uniformity: Medium. Brix content: 19° Brix. Size: Diameter: 0.72 inches (18 mm). Length: 0.8 inches (20 mm). Skin color: Red: 5R 5/8. Yellow green background color: 2.5GY 8/5. Pedicel: Length: 0.28 inches (7 mm). Diameter: 0.04 inches (1 mm). Color: 2.5 GY 7/6. Strength of attachment to berry: Very strong.

Berry flesh:

*Color*.—2.5GY 8/4.

*Juice, color*.—Clear.

*Juice production*.—Medium.

*Thickness of skin*.—Medium.

*Flavor*.—Neutral.

*Fragrance*.—None.

*Texture*.—Firm.

*Seeds*.—Rudimentary seeds present but very small and soft, not detectable when eating fruit.

*Use*.—Table Grape.

Disease and insect resistance: Typical of species.

I claim:

1. A new and distinct variety of grapevine plant named 'Royal Red', and parts thereof, substantially as illustrated and described herein.

* * * * *